United States Patent

Okazaki et al.

[11] Patent Number: 5,905,030
[45] Date of Patent: May 18, 1999

[54] METHOD AND APPARATUS FOR ASSAYING ENZYMATIC REACTION

[75] Inventors: Shigetoshi Okazaki; Hiroyuki Matsumoto, both of Shizuoka, Japan

[73] Assignee: Laboratory of Molecular Biophotonics, Shizuoka, Japan

[21] Appl. No.: 09/077,928
[22] PCT Filed: Feb. 24, 1997
[86] PCT No.: PCT/JP97/00513
§ 371 Date: Jun. 5, 1998
§ 102(e) Date: Jun. 5, 1998
[87] PCT Pub. No.: WO97/32198
PCT Pub. Date: Aug. 4, 1997

[30] Foreign Application Priority Data

Feb. 28, 1996 [JP] Japan ................................. 8-041805

[51] Int. Cl.$^6$ .............................. C12Q 1/34; C12Q 1/00
[52] U.S. Cl. ............................... 435/18; 435/4; 435/19; 435/283.1; 435/288.1; 422/55; 422/50; 422/82.05
[58] Field of Search .................... 435/18, 4, 19, 435/283.1, 288.1; 422/55, 50, 82.05

[56] References Cited

U.S. PATENT DOCUMENTS 4,022,667  5/1977  Myrick et al. ............................ 435/18

FOREIGN PATENT DOCUMENTS

| 0714024 | 5/1996 | European Pat. Off. . |
|---|---|---|
| 63-263446 | 10/1988 | Japan . |
| 560686 | 3/1993 | Japan . |
| 6102177 | 4/1994 | Japan . |
| 6242005 | 9/1994 | Japan . |

OTHER PUBLICATIONS

Imahori et al., "Dictionary of Biochemistry", K.K. Tokyo Kagaku Dojin (Tokyo), Apr. 10, 1984, refer to Lipase section.

"Furie Henkan Sekigaibunkoho (Fourier Transform Infrared Spectroscopy)," Gakkai Shuppan Center, (1985), pp. 163–171). (Partial Translation).

Primary Examiner—Louise N. Leary
Attorney, Agent, or Firm—Leydig, Voit & Mayer

[57] ABSTRACT

A method and apparatus for measuring enzyme activity by supplying a substrate solution and an enzyme solution into a reaction vessel combined with a total reflection absorption prism is disclosed. A measurement solution (40) in which the enzyme solution and the substrate solution are combined together is kept at a constant temperature within the reaction vessel (26) by a temperature control unit (23), and is stirred by a stirrer (21). Infrared light (36) emitted from an infrared light source (3) is made incident on the interface between a total reflection absorption prism (28) disposed in contact with the measurement solution (40) and the measurement solution (40) from the side of the total reflection absorption prism (28) and is totally reflected by the interface. The spectrum of transmitted infrared light (37) thus totally reflected and emitted is detected by an infrared light detector (5). According to thus detected spectrum, a change in the infrared absorption spectrum or absorbance is determined, whereby the enzyme reaction in the measurement solution (40) is measured.

7 Claims, 5 Drawing Sheets

METHOD AND APPARATUS FOR ASSAYING ENZYMATIC REACTION

TECHNICAL FIELD

The present invention relates to an enzyme reaction measuring method and its measuring apparatus in which a substrate solution and an enzyme solution are supplied into a reaction vessel so as to effect a reaction, and this enzyme reaction is continuously observed by infrared spectrometry.

BACKGROUND ART

Enzymes, which are a kind of catalyst produced by organisms, are mainly composed of proteins. Reaction materials of reactions catalyzed by the enzymes are known as substrates. For substantially all the reactions within living organisms, there exist enzymes corresponding thereto; and their enzyme reactions are performed under moderate conditions within the living organisms, thereby contributing to the maintenance of life. Accordingly, since a reduction in the action of an enzyme (enzyme activity) may cause a disease, it is prevalent in clinical tests to diagnose diseases by measuring activities of some kinds of enzymes in blood and urine.

Also, enzyme reactions are highly substrate-specific and are widely used as an energy-saving industrial process. For example, in fat and oil chemical industry, lipase is used for decomposing fats and oils. Lipase is an enzyme which hydrolyzes glycerol esters (triglycerides) of long-chain fatty acids. Lipase within alimentary canals mainly derives from the pancreas, though part thereof is secreted by the stomach and intestines. Lipase activity in blood has been known to rise in pancreatic diseases. Accordingly, the lipase activity in blood is measured to evaluate pancreatic diseases.

Measuring an enzyme reaction includes measuring quantitative and temporal changes in the substrate, which is a reaction material of the reaction catalyzed by the enzyme, and in a product generated by the reaction. Namely, the greater the ratio by which the substrate changes into the product, the higher the enzyme activity becomes. On the other hand, the smaller the ratio is, the lower the enzyme activity becomes. Also, when the change from the substrate to the product is measured over time, the reaction speed of the enzyme reaction can be analyzed.

Conventionally, in methods of measuring quantitative changes in the substrate and product, differences in physical or chemical properties of the substrate and product are utilized, so as to measure their respective quantitative changes. Examples thereof include: (1) a method in which the substrate or product is specifically caused to develop a color after the termination of the enzyme reaction, and is subjected to colorimetric determination, whereby the amount of increase or decrease in the substrate or product is determined (colorimetric determination method); (2) a method in which a compound labeled with a radioisotope (radioactive compound) is used as a substrate, the fact that the product generated by the enzyme reaction becomes a different radioactive compound is used to separate the radioactive compounds from each other, and the quantity of radioactivity is measured, whereby the amount of increase or decrease in the substrate or product is determined; (3) a fatty acid generated by the enzyme reaction is neutralization-titrated after the termination of the enzyme reaction (titration method); (4) a method in which the substrate is suspended in water, and the change in turbidity of the substrate solution upon decomposition of the substrate by the enzyme reaction is measured, whereby the amount of increase or decrease in the substrate or product is determined (turbidity measurement method); (5) a method in which, by utilizing spectroscopic differences between the substrate and product, wavelengths of light specifically absorbed by their respective materials (absorption wavelengths) are used, whereby the amount of increase or decrease in the substrate or product is determined from change in absorbance (spectroscopic measurement method); and the like. Among them, in particular, the spectroscopic measurement method and turbidity measurement method can continuously measure the enzyme reaction.

The above-mentioned measuring methods respectively have the following problems, however. First, in the colorimetric determination method, a color-producing reagent must react with the substrate or product to specifically color the same after the termination of the enzyme reaction. This complicates the operation and taking time for measurement, and the enzyme reaction cannot be measured continuously. Further, when the substrate is an aqueous suspension, it is difficult to transmit light therethrough, thus being problematic in that measurement cannot be fully performed.

In the method using the radioisotope, since the substrate or the product is separated after the termination of the enzyme reaction so as to measure the quantity of radioactivity, the operation is complicated, the measurement takes time, and the enzyme reaction cannot be measured continuously. Also, since the radioisotope is used, security and restriction are problems on the site of use.

Though the substrate and the product can be measured without separation after the termination of the enzyme reaction in the titration method, it is problematic in that the enzyme reaction cannot be measured continuously.

Though the turbidity measurement method is easy to operate and can continuously measure the enzyme reaction, the light scattered from the suspended substrate is measured and not the substrate itself. Since the enzyme reaction itself is not observed, this method is problematic in terms of reliability.

By contrast, the spectroscopic measurement method is a useful means in that the enzyme reaction can be measured easily and continuously without separating the substrate or product. Nevertheless, in the case where the solution to be measured has a turbidity, when the substrate is not water-soluble in particular, it is problematic in that quantitative measurement is difficult. It has not conventionally been applied to a turbid sample in such an aqueous solution. The influence of the above-mentioned turbidity is strong in particular when the measurement wavelength is within the range from ultraviolet to visible. Though the turbidity becomes less influential when the measurement wavelength is that of infrared light, it has been known that, since the absorption of water as a solvent is so much in the infrared range, it is necessary to use a cell having a thickness on the order of several hundred microns or use total reflection absorption method (Jiro Hiraishi ed., "Furie Henkan Sekigaibunkoho (Fourier Transform Infrared Spectroscopy)," Gakkai Shuppan Center, (1985), pp. 163–171).

When the spectroscopic measurement method is applied to an enzyme reaction, strict stirring is necessary due to the dependence of the enzyme reaction on the stirring speed and the like. In the above-mentioned cell having a thickness on the order of several hundred microns, however, stirring has been impossible. Further, typical measuring apparatus for the total reflection absorption method have failed to correctly measure enzyme activity since stirring cannot be effected therein.

In order to eliminate the above-mentioned essential problems resulting from spectroscopic measurement method, it is an object of the present invention to provide an enzyme reaction measuring method and its measuring apparatus in which it is unnecessary for the substrate and the product to be separated from each other, operation is easy, enzyme reactions can be measured continuously, and enzyme reactions can be measured with a high reliability.

DISCLOSURE OF THE INVENTION

The enzyme reaction measuring method in accordance with the present invention comprises the steps of: stirring a measurement solution containing an enzyme and a substrate at a predetermined temperature; making infrared light incident on an interface between a total reflection absorption prism disposed in contact with the measurement solution and the measurement solution from the side of the total reflection absorption prism and totally reflected thereby; and measuring a spectrum of thus totally reflected infrared light so as to determine a change in an infrared absorption spectrum or absorbance, from which an enzyme reaction in the measurement solution is measured.

As a consequence, even in the case where the measurement solution has a turbidity or the case where the substrate is not water-soluble, without separating the substrate and the product from each other, the enzyme reaction can be measured continuously with a high reliability in a simple operation.

Here, the enzyme catalyzes a hydrolysis reaction of an ester bond, and is a carboxylic acid ester hydrolase or lipase.

The enzyme reaction measuring apparatus in accordance with the present invention comprises a reaction vessel for accommodating a measurement solution in which a substrate solution and an enzyme solution are mixed together; substrate solution supplying means for supplying the substrate solution into the reaction vessel; enzyme solution supplying means for supplying the enzyme solution into the reaction vessel; temperature control means for controlling temperature of the measurement solution; stirring means for stirring the measurement solution; a total reflection absorption prism disposed in contact with the measurement solution; an infrared light source for making infrared light incident on the total reflection absorption prism such that the infrared light is totally reflected by an interface between the total reflection absorption prism and the measurement solution; infrared light detecting means for measuring a spectrum of the infrared light emitted from the total reflection absorption prism; and an arithmetic section for determining a change in an infrared absorption spectrum or absorbance according to the spectrum of the infrared light measured by the infrared light detecting means, so as to measure an enzyme reaction in the measurement solution.

As a consequence, the substrate solution and enzyme solution supplied to the reaction vessel respectively from the substrate solution supplying means and enzyme solution supplying means are mixed within the reaction vessel so as to yield the measurement solution, which is controlled by the temperature control means to a predetermined temperature and is stirred by the stirring means. The infrared light emitted from the infrared light source is made incident on the interface between the total reflection absorption prism disposed in contact with the measurement solution and the measurement solution from the total reflection absorption prism side and is totally reflected by the interface. The spectrum of the infrared light emitted from the total reflection absorption prism after the total reflection is measured by the infrared detecting means. Then, the arithmetic section determines the change in the infrared absorption spectrum or absorbance, thereby measuring the enzyme reaction in the measurement solution. Accordingly, even in the case where the measurement solution has a turbidity or the case where the substrate is not water-soluble, without separating the substrate and the product from each other, the enzyme reaction can be measured simply and continuously with high reliability.

The enzyme reaction measuring apparatus in accordance with the present invention further comprises solution discharging means for discharging the measurement solution in the reaction vessel, and cleaning liquid supplying means for supplying into the reaction vessel a cleaning liquid for cleaning the inside of the reaction vessel. As a consequence, after the measurement of one enzyme reaction is terminated, the measurement solution in the reaction vessel is discharged by the solution discharging means, and the inside of the reaction vessel is washed with the cleaning liquid supplied by the cleaning liquid supplying means, thus allowing the next enzyme reaction to be measured in succession.

With regard to the total reflection absorption prism, at least a region in contact with the measurement solution is preferably coated with Teflon (polytetrafluoroethylene). As a consequence, the substrate in the measurement solution is prevented from being deposited on the total reflection absorption prism.

BEST MODES FOR CARRYING OUT THE INVENTION

The present invention will be explained with reference to the accompanying drawings for further details.

Figure 1:
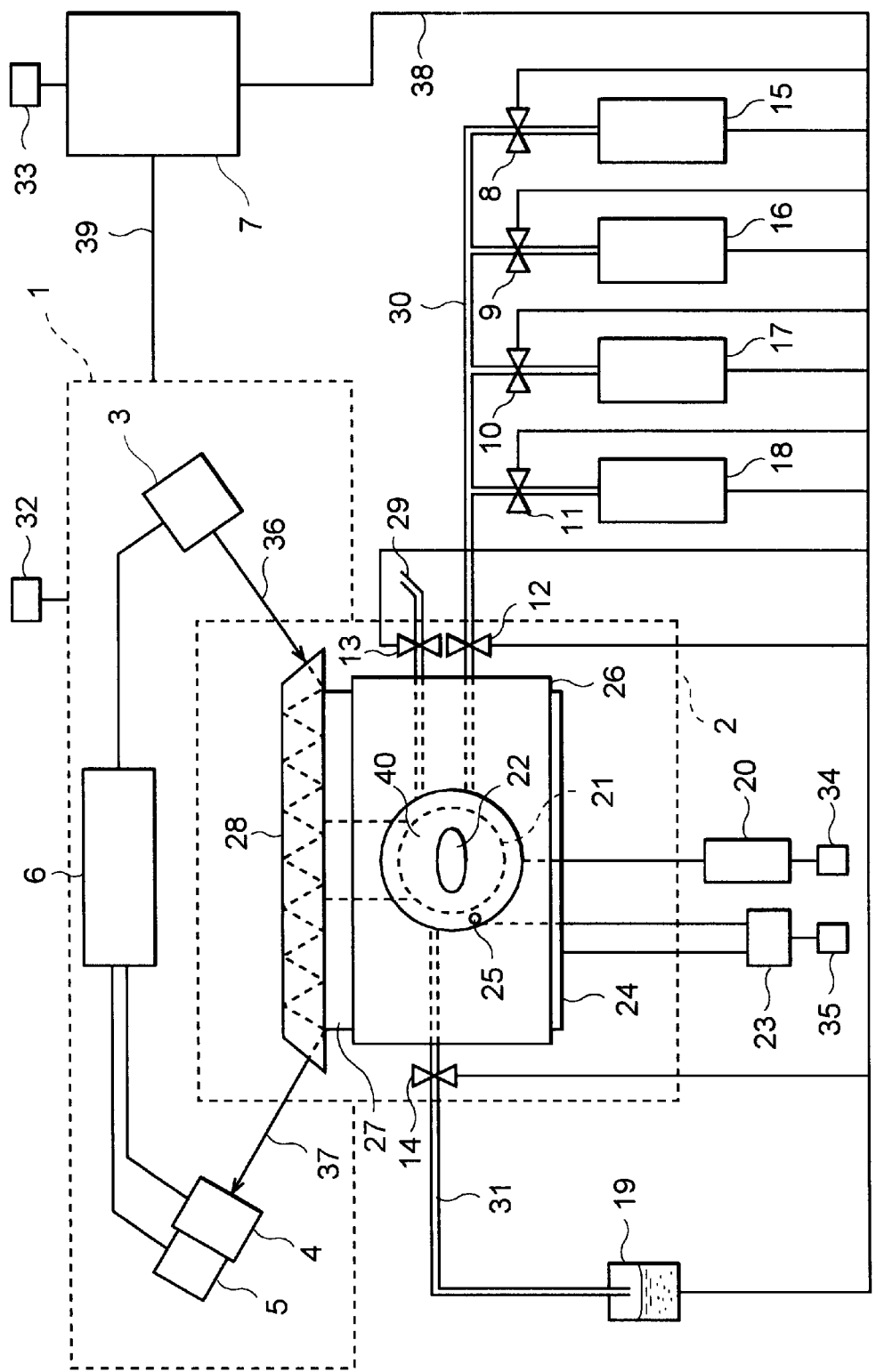
FIG. 1 is a configurational view of an enzyme reaction measuring apparatus in accordance with the present invention.

FIG. 1 is a configurational view showing an embodiment of the enzyme reaction measuring apparatus in accordance with the present invention. In order to clarify the configuration of this apparatus, a reaction vessel 26 is represented in section. Though this embodiment shows an infrared spectrophotometer using a spectroscope, a Fourier transform type infrared spectrophotometer or a combination of a light source emitting only an aimed wavelength of light and a detector may also be used.

This enzyme reaction measuring apparatus is mainly composed of an infrared spectrophotometer main body 1 and an infrared spectrophotometer sample chamber 2, and further comprises respective supply sections 15 to 18 for cleaning liquid, substrate solution, enzyme solution, and stop liquid. The infrared spectrophotometer main body 1 incorporates therein an infrared light source 3, a spectroscope 4, an infrared light detector 5, and a control section 6 for controlling them. The infrared spectrophotometer sample chamber 2 mainly incorporates therein the reaction vessel 26 and a total reflection absorption prism 28.

The infrared light source 3 is a light source for emitting infrared light. Infrared incident light 36 emitted from the infrared light source 3 is made incident on the entrance surface of the total reflection absorption prism 28. In the total reflection absorption prism 28, the upper surface and the lower surface (surface facing the reaction vessel 26) are in parallel to each other, whereas the entrance surface and exit surface are formed as being inclined relative thereto. The infrared light incident on the entrance surface of the total reflection absorption prism 28 propagates through the total reflection absorption prism 28 while repeating total reflection between the upper and lower surfaces thereof, so as to be emitted out of the exit surface.

The total reflection absorption prism 28 is most preferably made of ZnSe which has a large refractive index, but also is preferably made of Ge or Si. The angle of incidence of the infrared light onto the lower surface of the total reflection absorption prism 28 is preferably within the range of 40 to 60 degrees, most preferably at 45 degrees. Here, the smaller the difference between the refractive index of the total reflection absorption prism 28 and the refractive index of the measurement solution 40, the deeper becomes the penetration of evanescent waves generated in the measurement solution 40 when the infrared light is totally reflected by the lower surface of the total reflection absorption prism 28, whereby the infrared absorption spectrum caused by the substrate is enhanced.

Preferably, of the lower surface of the total reflection absorption prism 28, at least the region in contact with the measurement solution 40 is coated with Teflon. As a consequence of such a Teflon coating, the substrate in the measurement solution 40 can be prevented from being deposited on the total reflection absorption prism 28. Here, the depth of the penetration of evanescent waves generated in the measurement solution 40 when the infrared light is totally reflected by the lower surface of the total reflection absorption prism 28 is on the order of $\frac{1}{5}$ to $\frac{1}{7}$ of the wavelength of infrared light. Since the aimed wavelength is about 7 $\mu$m, in order for evanescent waves of infrared light to reach the measurement solution 40, it is necessary for the Teflon coating to have a thickness of several hundred nm or less.

Infrared transmitted light 37 emitted from the exit surface of the total reflection absorption prism 28 is made incident on the spectroscope 4. The spectroscope 4 selects the aimed or desired wavelength component of the infrared transmitted light 37. The infrared light detector 5 detects this aimed or desired wavelength component, and outputs a signal corresponding to the intensity thereof. The signal detected by the infrared light detector 5 is transferred to an arithmetic/control computer 7 by way of the control section 6 and a data transfer line 39. A power supply 32 is provided in order to supply electric power to each of the infrared light source 3, spectroscope 4, infrared light detector 5, and control section 6 within the infrared spectrophotometer main body 1.

The total reflection absorption prism 28 is attached to the reaction vessel 26 by way of a packing 27, whereby a part of the region of the lower surface of the total reflection absorption prism 28 comes into contact with the measurement solution 40 accommodated in the reaction vessel 26. The center portion of the packing 27 is formed with an aperture for defining the area of the region where the total reflection absorption prism 28 and the measurement solution 40 are in contact with each other.

The packing 27 is preferably made of a material which exhibits no absorption within the wavelength range to be measured, i.e., material (made of silicone rubber or Teflon, for example) which includes neither ester group nor carboxyl group. The packing 27 may also be a silicone rubber type adhesive which bonds the total reflection absorption prism 28 and the reaction vessel 26 together. Alternatively, of the lower surface of the total reflection absorption prism 28, the region other than that in contact with the measurement solution 40 may be vapor-deposited with a metal (e.g., aluminum, gold, or the like), and thus deposited film may be used as the packing 27.

The reaction vessel 26 is a vessel for accommodating the measurement solution (specifically, the substrate solution and enzyme solution). The side face of the reaction vessel 26 in contact with the total reflection absorption prism 28 is formed with an aperture for bringing the measurement solution 40 and the lower surface of the total reflection absorption prism 28 into contact with each other. This aperture is positioned so as to align with that formed in the packing 27. The material of the reaction vessel 26 is preferably Teflon or aluminum whose surface is coated with Teflon. The inner space of the reaction vessel 26 and the inner space of the infrared spectrophotometer sample chamber 2 are physically blocked from each other, whereby the measurement solution 40 and the infrared spectrophotometer sample chamber 2 would not directly come into contact with each other.

A stirring rotator 22 is disposed within the reaction vessel 26. The stirring rotator 22, which is used for stirring the measurement solution 40 at a constant speed in order to attain a constant condition for the enzyme reaction within the reaction vessel 26, is rotated according to an instruction from a magnetic stirrer main body 21, while its rotating speed is controlled by a magnetic stirrer control section 20 to a constant speed. A power supply 34 is used for supplying electric power to the magnetic stirrer control section 20.

The other side face of the reaction vessel 26 is provided with a panel heater 24. The panel heater 24 is used for keeping the measurement solution at a constant temperature in order to attain a constant temperature condition for the enzyme reaction within the reaction vessel 26. Also, a temperature sensor 25 is disposed within the reaction vessel 26. The temperature sensor 25 is used for measuring temperature of the measurement solution 40 within the reaction vessel 26. A temperature control unit 23 is used for controlling the panel heater 24 according the temperature of the measurement solution 40 within the reaction vessel 26 measured by the temperature sensor 25, so as to keep the temperature of the measurement solution 40 within the reaction vessel 26 at a predetermined level. A power supply 35 is used for supplying electric power to the temperature control unit 23.

Connected to the reaction vessel 26 are an air discharge section 29, a solution supply pipe 30, and a solution discharge pipe 31.

The air discharge section 29, which is used for discharging the air extruded from the inside of the reaction vessel 26 when various kinds of solutions are supplied therein, is lead from the inner space of the reaction vessel 26 to the outside of the infrared spectrophotometer sample chamber 2 by way of a solenoid valve 13 disposed therebetween.

The solution supply pipe 30 is a pipe for supplying each of the cleaning liquid, substrate solution, enzyme solution, and stop liquid. Connected to the solution supply pipe 30 by way of solenoid valves 8 to 11 further through a solenoid valve 12 are the cleaning liquid supply section 15 for supplying the cleaning liquid, substrate solution supply section 16 for supplying the substrate solution, enzyme solution supply section 17 for supplying the enzyme solution, and stop liquid supply section 18 for supplying the stop liquid, respectively.

The solution discharge pipe 31, which is a pipe for discharging the measurement solution 40 out of the reaction vessel 26, is connected to a solution discharge section 19 by way of a solenoid valve 14. The solution discharge section 19 draws therein the measurement solution 40 accommodated within the reaction vessel 26, thereby discharging the measurement solution 40.

The solenoid valves 8 to 14, cleaning liquid supply section 15, substrate solution supply section 16, enzyme solution supply section 17, stop liquid supply section 18, and solution discharge section 19 are connected to the arithmetic/control computer 7 by way of a control/power supply line 38 and are controlled by the arithmetic/control computer 7. A power supply 33 is used for supplying electric power to the arithmetic/control computer 7. Each of the cleaning liquid supply section 15, substrate solution supply section 16, enzyme solution supply section 17, and stop liquid supply section 18 is configured such that, according to an instruction from the arithmetic/control computer 7, it sends out a predetermined amount of its corresponding solution to the solution supply pipe 30 and sends out a predetermined amount of air or inactive gas (e.g., nitrogen gas or the like), so as to be able to quantitatively supply each solution into the reaction vessel 26 without leaving the solution within the solution supply pipe 30.

Figure 2:
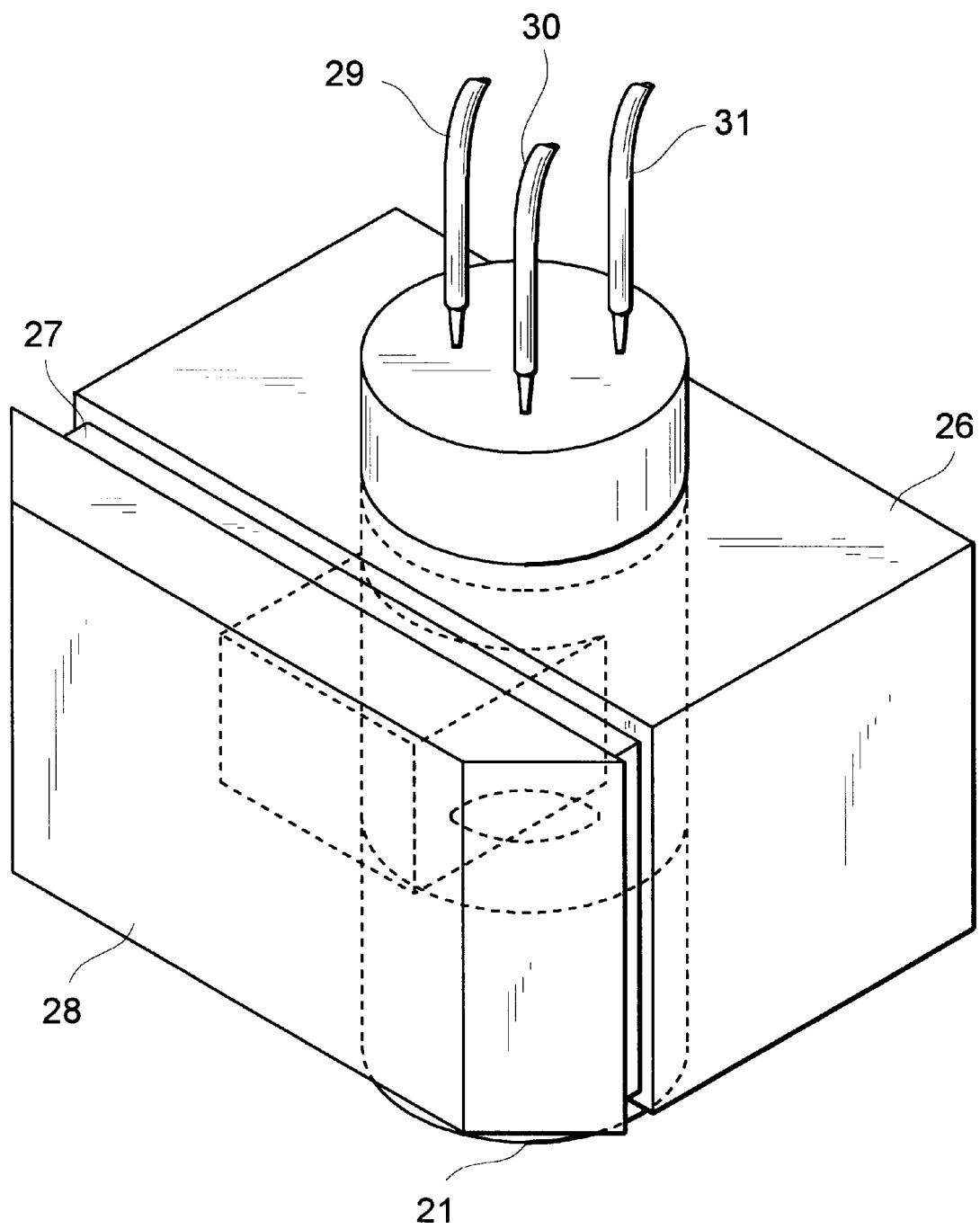
FIG. 2 is a perspective view of a reaction vessel in the above-mentioned apparatus.
Figure 3:
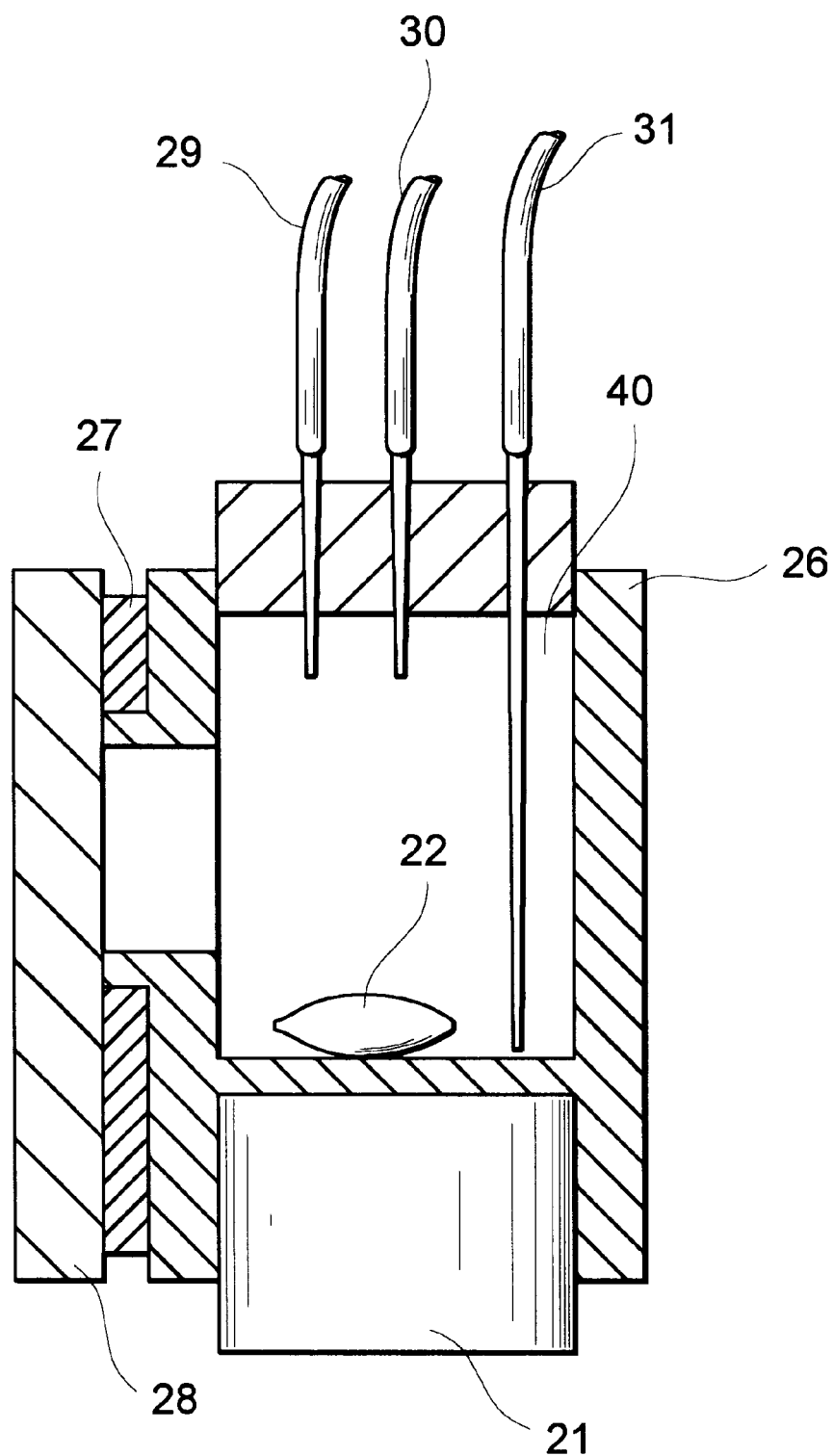
FIG. 3 is a sectional view of the reaction vessel in the above-mentioned apparatus.

FIG. 2 is a perspective view showing the reaction vessel 26, packing 27, and total reflection absorption prism 28 as viewed obliquely from thereabove; whereas FIG. 3 is a sectional view thereof taken along a plane perpendicular to the lower surface of the total reflection absorption prism 28. These drawings show the orientations of the reaction vessel 26, packing 27, and total reflection absorption prism 28 when they are actually disposed.

As shown in these drawings, one side face of the reaction vessel 26 is provided with an aperture, which is blocked by the Teflon-coated surface of the total reflection absorption prism 28. The lower part of the reaction vessel 26 is provided with the magnetic stirrer 21, whereas the stirring rotator 22 is disposed within the reaction vessel 26. The air discharge section 29, solution supply pipe 30, and solution discharge pipe 31 are lead into the inner space of the reaction vessel 26 from thereabove. Among them, the tips of the air discharge section 29 and solution supply pipe 30 are lead to the vicinity of the upper surface in the inner space of the reaction vessel 26, whereas the tip of the solution discharge pipe 31 is lead to the vicinity of the bottom surface in the inner space of the reaction vessel 26.

Figure 4:
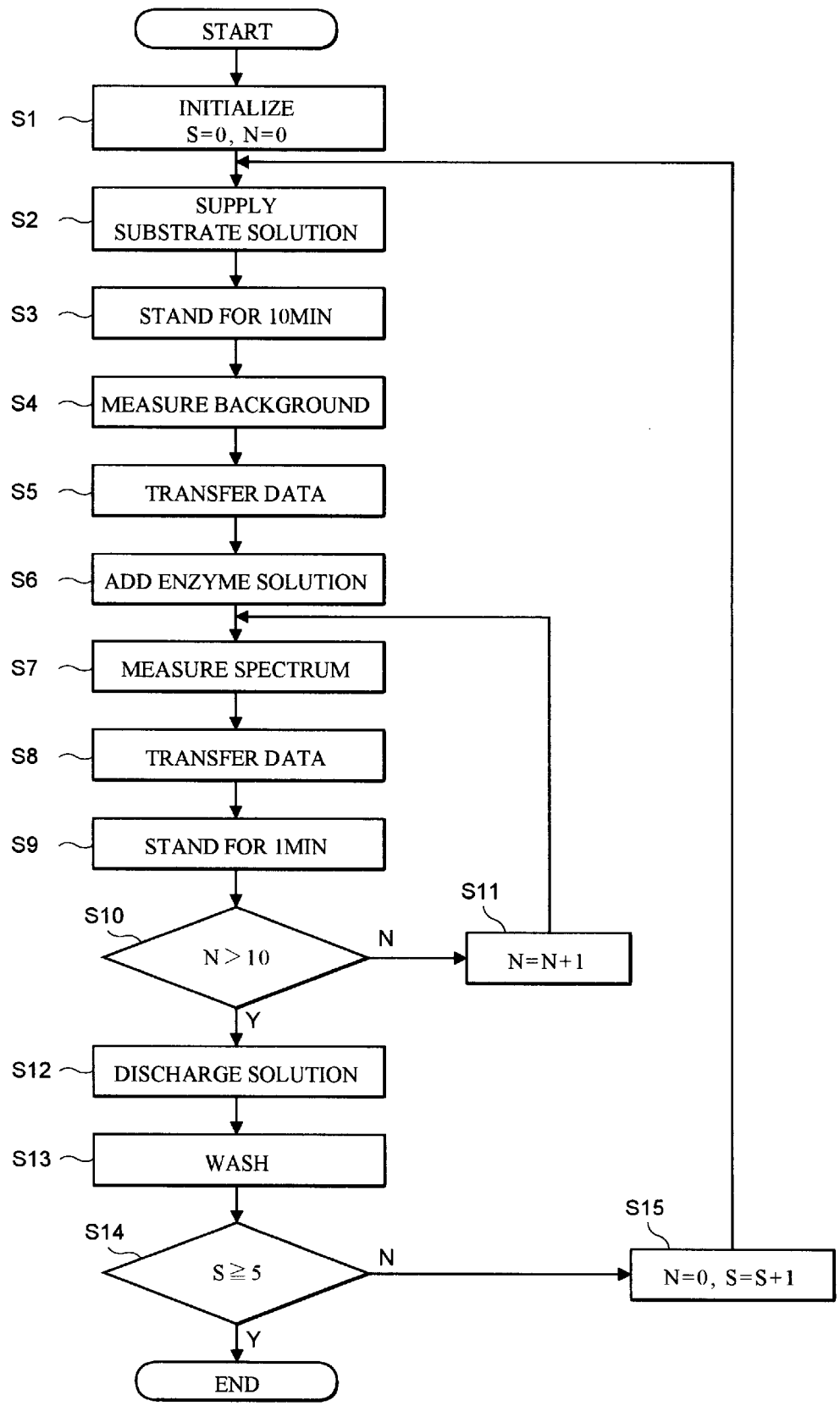
FIG. 4 is a flowchart of measuring operations of the above-mentioned apparatus.

In the following, an enzyme reaction measuring method using thus configured enzyme reaction measuring apparatus will be explained. FIG. 4 is an example of flowchart for measuring operations in the apparatus configured as mentioned above. The measuring operations will be hereinafter explained with reference to FIG. 4. Here, FIG. 4 is a flowchart in the case where the number of samples to be measured is 5, and the enzyme reaction for each sample is measured 11 times at intervals of 1 minute. Also, the following processing is effected according to instructions from the arithmetic/control computer 7.

First, at step S1, in order to effect stable measurement, all the power supplies 32 to 35 in the apparatus are turned on before starting the measurement, and the apparatus is initialized. Namely, the inside of the infrared spectrophotometer sample chamber 2 is purged with dry air or nitrogen beforehand, the reaction temperature within the reaction vessel 26 is set by the temperature control unit 23, and the stirring speed of the stirring rotator 22 is set by the magnetic stirrer control section 20. Also, in the arithmetic/control computer 7, a counter for counting the number of samples S and a counter for counting the number of measurements N each are initialized to a value of 0. At this point of time, all the solenoid valves 8 to 14 are in their closed state.

At subsequent step S2, the solenoid valves 13, 12, and 9 are opened, whereby a predetermined amount of a substrate solution is supplied from the substrate solution supply section 16 into the reaction vessel 26 through the solution supply pipe 30, and then a predetermined amount of nitrogen gas is supplied. After the predetermined amount of substrate solution is thus supplied into the reaction vessel 26, the solenoid valves 9 and 12 are closed. At step S3, the apparatus is allowed to stand for 10 minutes so that the substrate solution within the reaction vessel 26 attains a preset temperature.

At subsequent step S4, the infrared absorption spectrum of the substrate solution alone is measured as background. Namely, the infrared incident light 36 emitted from the infrared light source 3 is made incident on the entrance surface of the total reflection absorption prism 28 and is propagated through the total reflection absorption prism 28 while being totally reflected by the upper face and lower face thereof. Each wavelength component of the infrared transmitted light 37 emitted out of the exit surface of the total reflection absorption prism 28 is chosen by the spectroscope 4 and is detected by the infrared light detector 5.

Here, since the lower surface of the total reflection absorption prism 28 is in contact with the substrate solution within the reaction vessel 26, when the infrared light is totally reflected by the lower surface of the total reflection absorption prism 28, its evanescent waves are generated in the substrate solution. Also, as the infrared light repeats total reflection between the upper and lower surfaces of the total reflection absorption prism 28, the evanescent waves are generated over a wide area where the lower surface of the total reflection absorption prism 28 and the substrate solution are in contact with each other. Accordingly, the infrared transmitted light 37 emitted out of the exit surface of the total reflection absorption prism 28 is strongly influenced by absorption by the substrate solution. At step S5, thus obtained data of the infrared absorption spectrum are transferred to the arithmetic/control computer 7 by way of the control section 6.

At subsequent step S6, the solenoid valves 12 and 10 are opened, whereby a predetermined amount of an enzyme solution, which is a sample, is supplied from the enzyme solution supply section 17 into the reaction vessel 26 through the solution supply pipe 30, and then a predetermined amount of nitrogen gas is supplied, thus quantitatively supplying the enzyme solution into the reaction vessel 26. Thereafter, the solenoid valves 10 and 12 are closed.

At subsequent step S7, the infrared absorption spectrum of the measurement solution 40 in which the substrate solution and the enzyme solution are mixed together is measured. This measurement is substantially similar to that in the case of step S4. The subject of measurement at step S7, however, is the measurement solution, in which the substrate solution and the enzyme solution are mixed together, which is in a suspended state as being stirred by the stirring rotator 22 at a predetermined rotating speed. Even in such a case, when the infrared light is totally reflected by the lower surface of the total reflection absorption prism 28, its evanescent waves are generated within the measurement solution 40. In this case, the infrared transmitted light 37 emitted from the exit surface of the total reflection absorption prism 28 is under the influence of the substrate reduced by the reaction between the substrate and the enzyme.

At step S8, the spectrum data measured at step S7 are transferred to the arithmetic/control computer 7 by way of the control section 6. Then, the arithmetic/control computer 7 determines differences between thus transferred spectrum data and the background spectrum data that have already been transferred at step S5.

At subsequent step S9, the apparatus is allowed to stand for one minute. At step S10, the measurement number counter N and value 10 are compared with each other in terms of magnitude. If the measurement number counter N is 10 or less, then the operation proceeds to step S11; otherwise, it proceeds to step S12. At step S11, value 1 is added to the measurement number counter N, and then the operation returns to the spectrum measurement at step S7. Namely, in a loop constituted by steps S7 to S11, spectrum data concerning the measurement solution 40 are measured 11 times in total at intervals of 1 minute, and differences between thus measured spectrum data and the background spectrum data are determined.

At step S12, the solenoid valve 14 is opened, whereby the measurement solution within the reaction vessel 26 is discharged by the solution discharge section 19. At step S13, the solenoid valves 12 and 8 are opened, whereby the cleaning liquid is supplied from the cleaning liquid supply section 15 to the reaction vessel 26 through the solution supply pipe 30 and, after the inside of the reaction vessel 26 is fully washed, the solenoid valve 13 is closed. Then, a predetermined amount of nitrogen gas is supplied and, after the cleaning liquid is completely discharged out of the reaction vessel 26, the solenoid valves 8, 12, and 14 are closed. Measurement of one sample is thus completed.

At subsequent step S14, the sample number counter S and value 5 are compared with each other. If the sample number counters is less than value 5, the operation proceeds to step S15; otherwise, the measurement is completely terminated. At step S15, the measurement number counter N is set to value 0, value 1 is added to the sample number counter S, and the operation returns to step S2. Namely, in a loop constituted by steps S2 to S15, for each of 5 samples, spectrum data concerning the measurement solution 40 are measured 11 times in total at intervals of 1 minute, and differences between thus measured spectrum data and the background spectrum data are determined.

Accordingly, as the foregoing operations are performed, the arithmetic/control computer 7 obtains per-minute changes in infrared absorption spectrum caused by enzyme reactions due to enzymes in the 5 samples. From the amount of these changes, enzyme activity of each enzyme can be analyzed. Also, chemical kinetics analysis of each enzyme can be realized according to changes in infrared absorption spectrum over time.

In the following, the present invention will be specifically explained with reference to Examples, though the present invention should not be restricted the following Examples. Examples of enzyme reaction measurement effected by the above-mentioned apparatus will be shown hereinafter.

Reagents used are: (1) olive oil (special regent for lipase measurement) manufactured by Nakalai Tesque, Inc.; (2) polyvinyl alcohol (Kuraray POVAL, PVA-117) manufactured by Kuraray Co., Ltd.; (3) polyvinyl alcohol (Kuraray POVAL, PVA-205) manufactured by Kuraray Co., Ltd.; and (4) Lipase OF (360,000 U/g) manufactured by Meito Sangyo Co., Ltd.

A polyvinyl alcohol solution was prepared as follows. Namely, 18.5 g of polyvinyl alcohol (Kuraray POVAL, PVA-117) and 1.5 g of polyvinyl alcohol (Kuraray POVAL, PVA-205) were mixed with about 500 ml of Milli-Q water, and the resulting mixture was stirred by a stirrer. Thereafter, the mixture was autoclaved (at 120° C. for 2 to 3 minutes), and was further stirred by the stirrer so as to be completely dissolved. After this mixture liquid was cooled to room temperature, Milli-Q water was added thereto so that the total became 1 liter. After further being stirred, the mixture liquid was filtered and stored at room temperature.

A buffer for enzyme solution (0.1-M phosphate buffer) was prepared as follows. Namely, 2.4 g of sodium dihydrogen phosphate (anhydride) were dissolved in Milli-Q water, thereby finally yielding 200 ml of Milli-Q water. Also, 7.1 g of disodium hydrogen phosphate (anhydride) were dissolved in Milli-Q water, thereby finally yielding 500 ml of Milli-Q water. Then, the above-mentioned 200 ml of sodium dihydrogen phosphate solution were placed in a beaker having a volume of 500 ml or 1 liter and set to a pH meter. The disodium hydrogen phosphate solution was further added thereto such that pH became 7.0. The resulting solution was filtered and then was stored under refrigeration.

An olive oil emulsion was prepared as follows. Namely, 20 ml of olive oil (special reagent for lipase measurement) and 60 ml of polyvinyl alcohol solution were metered and were taken into a container having a volume of 150 ml. The resulting mixture was stirred by a stirrer (for 10 minutes at 2,000 rpm) while the container was surrounded by ice and cooled thereby. Thereafter, the mixture was allowed to stand for an hour while being cooled with ice.

An enzyme solution was prepared as follows. Namely, 0.028 g of Lipase OF (360,000 U/g) was weighed and taken into a plastic test tube having a volume of 10 ml. With 10 ml of the enzyme solution buffer being added thereto, the test tube was inverted to effect mixing (1,000 U/ml) without bubbling.

For each of thus prepared substrate solution (olive oil emulsion solution and enzyme solution buffer) and enzyme solution, the enzyme reaction was measured by the enzyme reaction measuring apparatus and method in accordance with this embodiment. The temperature of the measurement solution within the reaction vessel 26 was set to 37° C. by the temperature control unit 23, panel heater 24, and temperature sensor 25. The stirring speed of the stirring rotator 22 was set to about 1,000 rpm by the magnetic stirrer control section 20 and the magnetic stirrer main body 21.

First, as the substrate solution, 2 ml of the olive oil emulsion solution and 1.6 ml of the enzyme solution buffer were supplied into the reaction vessel 26. After they were allowed to stand for 10 minutes, background was measured, whereby background spectrum data were obtained. Then, 0.4 ml of enzyme solution was supplied into the reaction vessel 26, and spectrum was measured in total of 21 times at intervals of 1 minute over the period of 20 minutes, whereby infrared absorption spectrum data were obtained.

Figure 5:
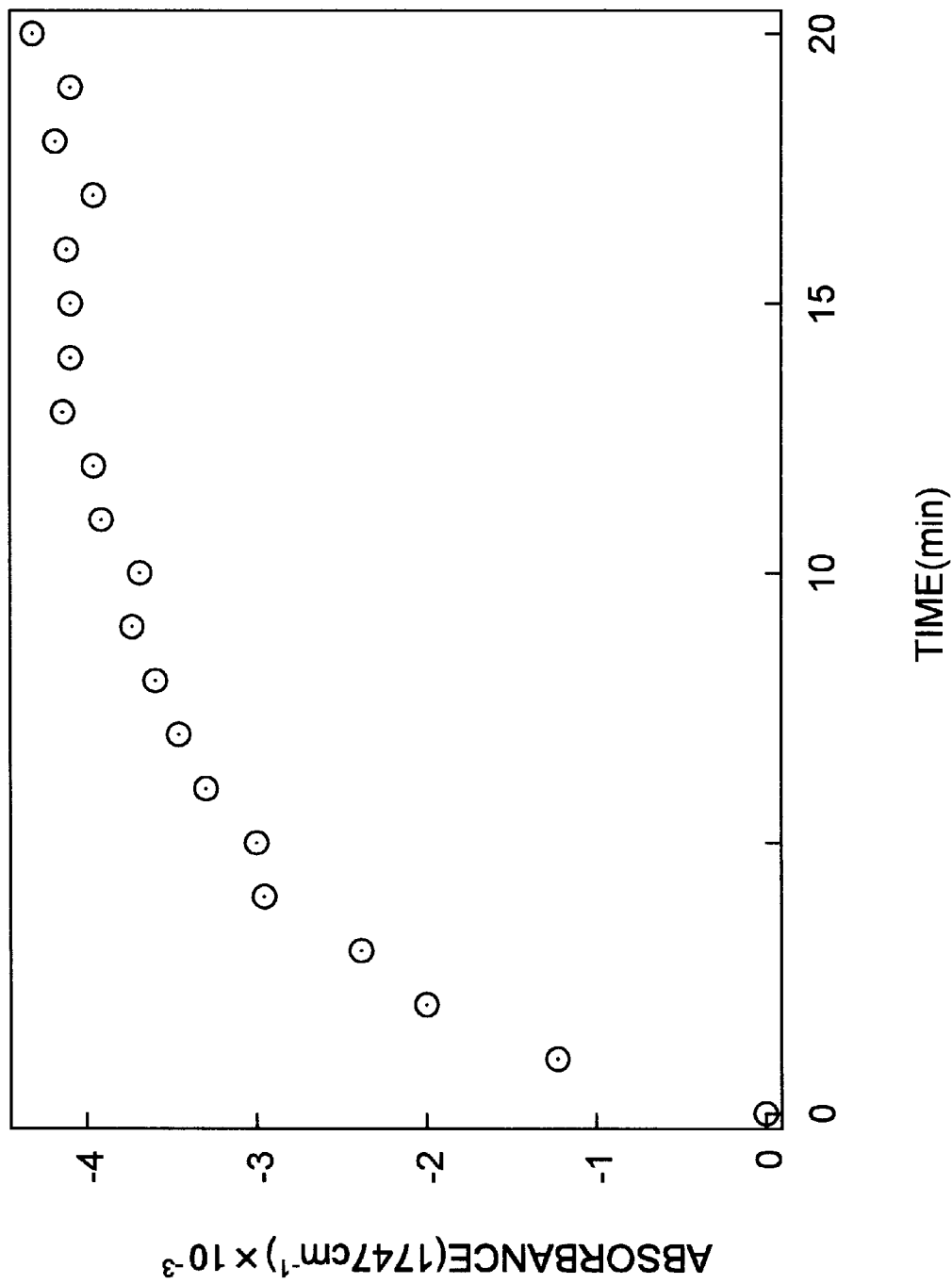
FIG. 5 is a chart showing results of a hydrolysis reaction of olive oil by lipase, obtained by use of the above-mentioned apparatus.

From the infrared absorption spectrum data concerning the measurement solution in which the enzyme solution and the substrate solution are mixed together, the background spectrum data are subtracted. The reaction speed of the enzyme reaction is obtained according to the result thereof. FIG. 5 shows changes in absorbance at a wave number of 1,745 $cm^{-1}$ in the infrared absorption spectrum from which background has been subtracted. The result of measurement obtained by the enzyme reaction measuring apparatus in accordance with this embodiment accords well with the result separately measured by titration method, thus indicating that the enzyme reaction can be measured by use of this apparatus.

INDUSTRIAL APPLICABILITY

As explained in the foregoing, in the enzyme reaction measuring method and its measuring apparatus in accordance with the present invention, even in the case where the measurement solution has a turbidity or the case where the substrate is not water-soluble, without separating the substrate and the product from each other, the enzyme reaction can be measured simply and continuously with high reliability. Accordingly, the enzyme reaction measuring method and its measuring apparatus in accordance with the present invention are suitably used for diagnosing diseases by measuring some kinds of enzyme activities in blood or urine and judging pancreatic diseases by measuring lipase activity in blood in the sites of clinical tests, and for measuring the reaction speed of a fat or oil and lipase in an industrial process in the fat and oil chemical industry or the like.

We claim:

1. An enzyme reaction measuring method comprising the steps of: stirring a measurement solution containing an enzyme and a substrate at a predetermined temperature; making infrared light incident on an interface between a total reflection absorption prism disposed in contact with said measurement solution and said measurement solution from a side of said total reflection absorption prism and totally reflected thereby; and measuring a spectrum of the thus totally reflected infrared light so as to determine a change in an infrared absorption spectrum or absorbance, from which an enzyme reaction in said measurement solution is measured.

2. The enzyme reaction measuring method according to claim 1, wherein said enzyme catalyzes a hydrolysis reaction of an ester bond.

3. The enzyme reaction measuring method according to claim 2, wherein said enzyme is a carboxylic acid ester hydrolase.

4. The enzyme reaction measuring method according to claim 2, wherein said enzyme is lipase.

5. An enzyme reaction measuring apparatus comprising:
a reaction vessel for accommodating a measurement solution in which a substrate solution and an enzyme solution are mixed together;
a substrate solution supplying means for supplying said substrate solution into said reaction vessel;
an enzyme solution supplying means for supplying said enzyme solution into said reaction vessel;
a temperature control means for controlling the temperature of said measurement solution;
a stirring means for stirring said measurement solution;
a total reflection absorption prism disposed in contact with said measurement solution;
an infrared light source for making infrared light incident on said total reflection absorption prism such that said infrared light is totally reflected by an interface between said total reflection absorption prism and said measurement solution;
an infrared light detecting means for measuring a spectrum of said infrared light emitted from said total reflection absorption prism; and
an arithmetic section for determining a change in an infrared absorption spectrum or absorbance according to said spectrum of said infrared light measured by said infrared light detecting means, so as to measure an enzyme reaction in said measurement solution.

6. The enzyme reaction measuring apparatus according to claim 5, further comprising:
a solution discharging means for discharging said measurement solution in said reaction vessel; and
a cleaning liquid supplying means for supplying into said reaction vessel a cleaning liquid for cleaning the inside of said reaction vessel.

7. The enzyme reaction measuring apparatus according to claim 5, wherein said total reflection absorption prism is coated with Teflon at least at a region in contact with said measurement solution.

* * * * *